United States Patent
Kim et al.

(10) Patent No.: US 9,284,344 B2
(45) Date of Patent: Mar. 15, 2016

(54) OLIGONUCLEOTIDE SYNTHESIS METHOD USING HIGHLY DISPERSIBLE LIQUID-PHASE SUPPORT

(75) Inventors: Shokaku Kim, Fuchu (JP); Masanori Matsumoto, Tsukuba (JP)

(73) Assignee: HOKKAIDO SYSTEM SCIENCE CO., LTD., Sapporo-shi (JP)

( * ) Notice: Subject to any disclaimer, the term of this patent is extended or adjusted under 35 U.S.C. 154(b) by 0 days.

(21) Appl. No.: 14/404,562

(22) PCT Filed: May 30, 2012

(86) PCT No.: PCT/JP2012/063921
§ 371 (c)(1),
(2), (4) Date: Nov. 28, 2014

(87) PCT Pub. No.: WO2013/179412
PCT Pub. Date: Dec. 5, 2013

(65) Prior Publication Data
US 2015/0112053 A1    Apr. 23, 2015

(51) Int. Cl.
C07H 21/00 (2006.01)
C07H 1/04 (2006.01)
C07H 1/02 (2006.01)
C07H 21/04 (2006.01)
C07H 21/02 (2006.01)
C07H 1/00 (2006.01)
C07H 19/073 (2006.01)

(52) U.S. Cl.
CPC .................. C07H 21/00 (2013.01); C07H 1/00 (2013.01); C07H 1/02 (2013.01); C07H 1/04 (2013.01); C07H 19/073 (2013.01); C07H 21/02 (2013.01); C07H 21/04 (2013.01)

(58) Field of Classification Search
None
See application file for complete search history.

(56) References Cited

U.S. PATENT DOCUMENTS

| 2002/0007048 A1 | 1/2002 | Koster et al. |
| 2002/0016451 A1 | 2/2002 | Koster et al. |
| 2012/0296074 A1 | 11/2012 | Hirai et al. |

FOREIGN PATENT DOCUMENTS

| EP | 2 711 370 A1 | 3/2014 |
| EP | 2 816 053 A1 | 12/2014 |
| JP | 2003 2895 | 1/2003 |
| JP | 2009 131095 | 6/2009 |
| JP | 2010 275254 | 12/2010 |
| WO | 99 55718 | 11/1999 |

OTHER PUBLICATIONS

Extended Search Report issued on Sep. 17, 2015 in European Patent Application No. 12877844.6.

Shokaku Kim, et al., "Liquid-Phase RNA Synthesis by Using Alkyl-Chain-Soluble Support", Chemistry—A European Journal, vol. 19, No. 26, XP055211240, Jun. 24, 2013, pp. 8615-8620.

Matsumoto, M., et al., "Solution-phase synthesis of oligonucleotides on hydrophobic nanoparticles using a highly dispersible liquid support", DAI 12 KAI The RNA Society of Japan Nenkai Yoshishu, p. 245, P-137, (Jul. 27, 2010).

Beaucage, S.L., et al., "Deoxynucleoside Phosphoramidites-A New Class of Key Intermediates for Deoxypolynucleotide Synthesis", Tetrahedron Letters, vol. 22, No. 20, pp. 1859-1962, (1981).

Koster, H., et al., "Polymer Support Oligonucleotide Synthesis-XV [1,2] Synthesis of Oligodeoxynucleotides on Controlled Pore Glass (CPG) Using Phosphate and a New Phosphite Triester Approach", Tetrahedron, vol. 40, No. 1, pp. 103-112, (1984).

Wright, P., et al., "Large Scale Synthesis of Oligonucleotides via Phosphoramidite Nucleosides and a High-loaded Polystyrene Support", Tetrahedron Letters, vol. 34, No. 21, pp. 3373-3376 (1993).

International Search Report Issued Jul. 3, 2012 in PCT/JP12/063921 Filed May 30, 2012.

*Primary Examiner* — Patrick Lewis
(74) *Attorney, Agent, or Firm* — Oblon, McClelland, Maier & Neustadt, L.L.P.

(57) ABSTRACT

A nucleic acid synthesis method enabling a reaction in a fluid (flow) with a highly dispersible liquid-phase support to improve coupling efficiency is provided.

The method for synthesizing an oligonucleotide comprising: sequentially condensing and oxidizing a nucleoside phosphoramidite compound in the presence of an acid/azole complex compound using a starting raw material, i.e., hydrophobic group-bonded nucleoside represented by Formula (1): where $R^1$: an alkylene group having 1 to 12 carbon atoms, $R^2$: an alkylene group having 1 to 22 carbon atoms, $R^3$ and $R^4$ each independently represent an alkyl group having 1 to 22 carbon atoms or the like, $R^5$: a single bond or an alkylene group having 1 to 22 carbon atoms, $R^6$: each independently an alkyl group having 6 to 30 carbon atoms, n represents an integer of 2 to 6, X represents a hydrogen atom, hydroxyl group, or the like, Y: a protecting group deprotectable under an acidic condition, and Z: an adenyl group, a guanyl group, or the like having a polar group optionally protected by a protecting group, wherein a condensation reaction is performed by preliminarily dissolving the hydrophobic group-bonded nucleoside or hydrophobic group-bonded oligonucleotide and the nucleoside phosphoramidite compound in a non-polar solvent, and contacting the resulting solution with the acid/azole complex compound or a solution containing the complex compound.

(1)

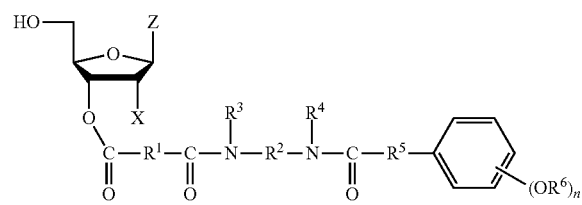

5 Claims, 3 Drawing Sheets

OLIGONUCLEOTIDE SYNTHESIS METHOD USING HIGHLY DISPERSIBLE LIQUID-PHASE SUPPORT

FIELD OF THE INVENTION

The present invention relates to an oligonucleotide synthesis method enabling a flow reaction with a highly dispersible liquid-phase support.

BACKGROUND OF THE INVENTION

A nucleic acid synthesis method at present mainly employs a solid-phase synthesis method according to a phosphoramidite method (Non Patent Literatures 1 to 3). In the phosphoramidite method, a 5'-hydroxyl group, an amino group of a base, and an amidite monomer having a protected 2'-hydroxyl group, if in RNA, are coupled with a promoter (activator) such as tetrazole compounds and imidazole compounds, and the resulting product is oxidized to form a phosphodiester bond (see the following formula):

= Nucleotide where the protecting group represents DMTr, MMTr or the like; the protected base represents Bz-adenine, Bz-cytosine, iBu-guanine, thymine, uracil, Pac-adenine, Ac-cytosine, iPr-Pac-guanine, dmf-guanine, another protected modified base, or the like; X represents H, O-TBDMS, O-Tom, O-Cpep, an O-cyanoethyl group, O—F, or the like; and Y represents a hydrogen atom, an ethylthio group, a benzylmercapto group, or the like.

In the solid-phase synthesis method, molecules are sequentially connected to a solid component such as controlled pore glass (CPG) or a cross-linked polystyrene resin through a linker. In this method, products are readily separated and refined for every reaction, and its procedure can be easily mechanized. For this reason, the solid-phase synthesis method can synthesize a small amount and a variety of products, such as a primer used in a PCR method in a short time, which is one of strong scientific techniques supporting the current biotechniques.

The synthetic nucleic acid has been extensively used not only in basic research in molecular biology, but also in medical applications such as nucleic acid medicines using antisense techniques in an RNAi method or in applications to electronic devices in engineering.

Especially applications to medicines require continuous supply of a large amount of high-quality synthetic nucleic acid.

Unfortunately, the solid-phase synthesis method using a solid-phase column fixes the production capacity to lose scalability in the reaction, which causes new problems in steps of the production process to give significant load on persons who develop the process. In particular, synthesis of RNA needs an expensive amidite reagent as a raw material, resulting in huge cost even in a demonstration test using a few grams of the reagent. Another problem is that the reaction yield is usually lower than that in a liquid-phase method. The solid-phase synthesis method is still unsatisfactory.

Under such circumstances, the present inventors developed a nucleoside derivative (hydrophobic group-bonded nucleoside) to which a highly dispersible liquid-phase support (HDLS) enabling control of high dispersion and aggregation due to the polarity of a solvent is bonded, found that the nucleoside derivative used as a starting raw material for synthesis of oligonucleotide can significantly reduce the amount of a reagent to be added and can significantly reduce complexities in separation and recovery operations typically found in the liquid-phase synthesis, and filed a patent application (Patent Literature 1).

CITATION LIST

Patent Literature

Patent Literature 1: Japanese Patent Application No. 2009-131095

Non Patent Literature

Non Patent Literature 1: S. L. Beaucage, M. H. Caruthers, Tetrahedron Lett., 22, 1859 (1981)
Non Patent Literature 2: H. Koster, et al. Tetrahedron, 40, 103 (1984)
Non Patent Literature 3: P. Wright, D. Lloyd, W. Rapp, A. Andrus, Tetrahedron Lett., 34, 3373 (1993)

SUMMARY OF INVENTION

Problems to be Solved by the Invention

The present invention relates to an oligonucleotide synthesis method enabling a reaction in a fluid (flow) with a highly dispersible liquid-phase support to improve coupling efficiency.

Means for Solving the Problem

The present inventors, who conducted research on the reaction conditions on the synthesis of oligonucleotide by use of the hydrophobic group-bonded nucleoside as a starting material, has found that coupling of a nucleoside phosphoramidite compound progresses with high efficiency to facilitate a reaction in flow by a procedure in a condensation reaction of preliminarily dissolving the hydrophobic group-bonded nucleoside or hydrophobic group-bonded oligonucleotide and the nucleoside phosphoramidite compound (amidite monomer) in a non-polar solvent, and contacting the resulting solution with an acid/azole complex compound or a solution containing the complex compound.

Namely, the present invention is directed to the following 1) to 5):

1) An oligonucleotide synthesis method, comprising a step of sequentially condensing and oxidizing a nucleoside phosphoramidite compound in the presence of an acid/azole complex compound using a starting raw material, i.e., hydrophobic group-bonded nucleoside represented by Formula (1):

(1)

where $R^1$ represents an alkylene group having 1 to 12 carbon atoms; $R^2$ represents an alkylene group having 1 to 22 carbon atoms; $R^3$ and $R^4$ each independently represent an alkyl group having 1 to 22 carbon atoms, or $R^3$ and $R^4$ represent a divalent group in which they are bonded to each other to form a heterocycle together with adjacent nitrogen atoms and $R^2$, the heterocycle being represented by Formula (2):

(2)

where $R^7$ represents an alkyl group having 1 to 6 carbon atoms; m represents an integer of 0 or 1; and y represents an integer of 0 to 3;
$R^5$ represents a single bond or an alkylene group having 1 to 22 carbon atoms; $R^6$ each independently represents an alkyl group having 6 to 30 carbon atoms; n represents an integer of 2 to 6; X represents a hydrogen atom, a hydroxyl group, or a hydroxyl group protected by a protecting group; and Z represents an adenyl group, a guanyl group, a cytosyl group, a thyminyl group, a uracil group, or a derivative of the nucleic acid base having a polar group optionally protected by a protecting group;
wherein a condensation reaction is performed by preliminarily dissolving the hydrophobic group-bonded nucleoside or hydrophobic group-bonded oligonucleotide and the nucleoside phosphoramidite compound in a non-polar solvent, and contacting the resulting solution with the acid/azole complex compound or a solution containing the complex compound.

2) The oligonucleotide synthesis method according to 1), wherein a dissolution solution of the hydrophobic group-bonded nucleoside or hydrophobic group-bonded oligonucleotide and the nucleoside phosphoramidite compound in a non-polar solvent and a dissolution solution of the acid/azole complex compound in a non-polar solvent are separately prepared, and are mixed.

3) The oligonucleotide synthesis method according to 1) or 2), wherein a dissolution solution of the hydrophobic group-bonded nucleoside or hydrophobic group-bonded oligonucleotide and the nucleoside phosphoramidite compound in a non-polar solvent and a dissolution solution of an acid/azole complex compound in a non-polar solvent are separately fed into a flow path to continuously conduct the condensation reaction in the flow path.

4) The oligonucleotide synthesis method according to 1) to 3), wherein the starting raw material hydrophobic group-bonded nucleoside is a compound represented by Formula (3):

(3)

where $R^{6'}$ each independently represents an alkyl group having 18 to 30 carbon atoms; and $R^1$, X, Z, and y represent the same as above.

5) The oligonucleotide synthesis method according to 4), wherein in Formula (3), $R^{6'}$ is an octadecyl group.

Effects of the Invention

The oligonucleotide synthesis method according to the present invention does not inhibit activation of the nucleoside phosphoramidite compound by the acid/azole complex compound (activator) in the condensation reaction, enables the condensation reaction in flow, and can produce oligonucleotide simply and efficiently. The oligonucleotide synthesis method according to the present invention can also produce RNA oligonucleotide, which is difficult to synthesize by a liquid-phase synthesis method in the related art, with high yield.

The dissolution solution of the hydrophobic group-bonded nucleoside or hydrophobic group-bonded oligonucleotide and the nucleoside phosphoramidite compound in a non-polar solvent and the dissolution solution of the acid/azole complex compound in a non-polar solvent are separately prepared, and are mixed. Such a two-solution mixing flow synthetic system can vary an amount of production only by an increase or decrease of the amounts of the two solutions, and can always maintain predetermined reaction efficiency by use of a small amount of a reagent to be added. This system is more useful than a batch type liquid-phase synthesis method and a solid-phase synthesis method. Advantageously, use of the hydrophobic group-bonded nucleoside can readily crystallize and solidify the reaction product with a high polar solvent to enable simple separation and refining as in a solid-phase method. Consequently, the oligonucleotide synthesis method according to the present invention is significantly useful in mass production of nucleic acid.

DESCRIPTION OF EMBODIMENT

The oligonucleotide synthesis method according to the present invention employs a starting raw material, i.e., hydrophobic group-bonded nucleoside represented by Formula (1):

(1)

where $R^1$ represents an alkylene group having 1 to 12 carbon atoms; $R^2$ represents an alkylene group having 1 to 22 carbon atoms; $R^3$ and $R^4$ each independently represent an alkyl group having 1 to 22 carbon atoms, or $R^3$ and $R^4$ represent a divalent group in which they are bonded to each other to form a heterocycle together with adjacent nitrogen atoms and $R^2$, the heterocycle being represented by Formula (2):

(2)

where $R^7$ represents an alkyl group having 1 to 6 carbon atoms; m represents an integer of 0 or 1; and y represents an integer of 0 to 3;

$R^5$ represents a single bond or an alkylene group having 1 to 22 carbon atoms; $R^6$ each independently represents an alkyl group having 6 to 30 carbon atoms; n represents an integer of 2 to 6; X represents a hydrogen atom, a hydroxyl group, or a hydroxyl group protected by a protecting group; and Z represents an adenyl group, a guanyl group, a cytosyl group, a thyminyl group, a uracil group, or a derivative of the nucleic acid base having a polar group optionally protected by a protecting group.

The hydrophobic group-bonded nucleoside has a predetermined hydrophobic group represented by:

where $R^2$, $R^3$, $R^4$, $R^5$, $R^6$, and n represent the same as above. The hydrophobic group functions as a support (highly dispersible liquid-phase support: HDLS) in a liquid phase to enable the synthesis reaction of oligonucleotide in a non-polar solvent under hydrophobic environments where no water exists. Therefore, activation of the nucleoside phosphoramidite compound used in the synthesis of oligonucleotide by the acid/azole complex compound (activator) is not inhibited. Accordingly, use of hydrophobic group improves the reaction yield, so that even the oligonucleotide which is difficult to synthesize by the liquid-phase synthesis method in the related art, such as decameric or higher oligonucleotide, can be produced with high yield.

The physical properties of the hydrophobic group-bonded nucleoside vary according to the polarity of the solvent. The hydrophobic group-bonded nucleoside is dissolved or highly dispersed in a relatively low polar solvent such as THF, dichloromethane, and toluene, and aggregates and precipitates in a high polar solvent such as methanol, acetonitrile, or water. Utilizing such properties, a low polar solvent is used as the reaction solvent to construct a reaction field for the liquid-phase reaction, and a high polar solvent is used to crystallize and solidify the reaction product, which enables simple separation and refining as in a solid-phase method.

In Formula (1), the alkylene groups represented by $R^1$, $R^2$, and $R^5$ and the alkyl groups represented by $R^3$, $R^4$, $R^6$, and $R^7$ each may be linear or branched, and are preferably linear.

The alkylene group represented by $R^1$ has 1 or more and 12 or less carbon atoms, preferably 1 to 6 carbon atoms. Specific examples thereof can include a methylene group, an ethylene group, a propylene group, an isopropylene group, a butylene group, a pentylene group, and a hexylene group. Among these, a methylene group, an ethylene group, and a hexylene group are preferred, and an ethylene group is more preferred.

The alkylene group represented by $R^2$ has 1 or more and 22 or less carbon atoms, preferably 2 to 12 carbon atoms. Specific examples thereof can include a methylene group, an ethylene group, a propylene group, an isopropylene group, a butylene group, a pentylene group, and a hexylene group. An ethylene group is preferred.

When $R^3$ and $R^4$ are each independently an alkyl group, the alkyl group preferably has 1 to 6 carbon atoms. Specific examples of $R^3$ and $R^4$ can include a methyl group, an ethyl group, a propyl group, an isopropyl group, a butyl group, a pentyl group, and a hexyl group.

When $R^3$ and $R^4$ are a divalent group in which they are bonded to each other to form a heterocycle together with adjacent nitrogen atoms and $R^2$, the heterocycle being represented by Formula (2), m is preferably 0. Specific examples of the alkyl group having 1 to 6 carbon atoms represented by $R^7$ can include a methyl group, an ethyl group, a propyl group, an isopropyl group, a butyl group, a pentyl group, and a hexyl group. A methyl group is preferred, and y is preferably an integer of 0 to 2.

Specific examples of the heterocycle to be formed can include homopiperazine, piperazine, cis-2,6-dimethylpiperazine, 2,5-dimethylpiperazine, and 2-methylpiperazine. Among these, 2,6-dimethylpiperazine, piperazine, and 2,5-dimethylpiperazine are preferred, and piperazine is particularly preferred.

The alkylene group for $R^5$ which represents a single bond or an alkylene group has 1 or more and 22 or less carbon atoms, and an alkylene group having 1 to 6 carbon atoms is preferred. Specific examples thereof can include a methylene group, an ethylene group, a propylene group, an isopropylene group, a butylene group, a pentylene group, and a hexylene group. $R^5$ is preferably a single bond, a methylene group, an ethylene group, and a hexene group, more preferably a single bond.

The alkyl groups represented by $R^6$ each independently have 6 or more and 30 or less carbon atoms where n is an integer of 2 or more and 6 or less. n is preferably 3 or more and 6 or less, more preferably 3. $R^6$ has preferably 18 to 30 carbon atoms. More preferably, $R^6$ is an octadecyl group having 18 carbon atoms. The substitution position of $R^6$, i.e., the alkyl group having 6 to 30 carbon atoms is preferably the 3rd-, 4th-, and 5th-positions with respect to $R^5$.

In a preferred combination of the alkyl or alkylene groups represented by $R^1$ to $R^5$, $R^1$ is an ethylene group, $R^3$ and $R^4$ are a divalent group in which they are bonded to each other to form piperazine together with adjacent nitrogen atoms and $R^2$, $R^5$ is a single bond, and $R^6$ is an alkyl group having 18 to 30 carbon atoms, as in Formula (3):

(3)

where $R^{6'}$ each independently represent an alkyl group having 18 to 30 carbon atoms; and $R^1$, X, Z, and y represents the same as above.

Particularly, among these compounds represented by Formula (3), compounds having an octadecyl group for $R^{6'}$ are preferred.

X represents a hydrogen atom, a hydroxyl group, or a hydroxyl group protected by a protecting group. Where X is a hydrogen atom, a pentose residue contained in the hydrophobic group-bonded nucleoside according to the present invention is a deoxyribose residue. For this reason, where X is a hydrogen atom, the hydrophobic group-bonded nucleoside according to the present invention is hydrophobic group-bonded deoxyribonucleoside, which can be used for synthesis of oligodeoxyribonucleotide. Similarly where X is a hydroxyl group or a hydroxyl group protected by a protecting group, the pentose residue contained in the hydrophobic group-bonded nucleoside according to the present invention is a ribose residue having an optionally protected hydroxyl group at the 2nd-position. For this reason, where X is a hydroxyl group or a hydroxyl group protected by a protecting group, the hydrophobic group-bonded nucleoside according to the present invention is hydrophobic group-bonded ribonucleoside having an optionally protected hydroxyl group at the 2nd-position of the ribose residue, which can be used for synthesis of oligoribonucleotide.

Examples of the protecting group which optionally protects the hydroxyl group at the 2nd-position of the ribose residue can include any protecting group which can be used as a protecting group for a hydroxyl group. Specific examples thereof can include a methyl group, a benzyl group, a p-methoxybenzyl group, a tert-butyl group, a methoxymethyl group, a 2-tetrahydropyranyl group, an ethoxyethyl group, an acetyl group, a pivaloyl group, a benzoyl group, a trimethylsilyl group, a triethylsilyl group, a tert-butyldimethylsilyl group, a [(triisopropylsilyl)oxy]methyl (Tom) group, and a 1-(4-chlorophenyl)-4-ethoxypiperidin-4-yl (Cpep) group. Among these, a trimethylsilyl group, a triethylsilyl group, a [(triisopropylsilyl)oxy]methyl (Tom) group, and a tert-butyldimethylsilyl group are preferred. From the viewpoint of economy and availability, a tert-butyldimethylsilyl group is particularly preferred.

Z is an adenyl group, a guanyl group, a cytosyl group, a thyminyl group, a uracil group, or a derivative thereof having a polar group optionally protected by a protecting group. Namely, for Z, any base known in the related art as nucleic acid bases for DNA and RNA and derivatives thereof having an optionally protected polar group can be used. Examples of the derivative can include an 8-bromoadenyl group, an 8-bromoguanyl group, a 5-bromocytosyl group, a 5-iodocytosyl group, a 5-bromouracil group, a 5-iodouracil group, a 5-fluorouracil group, a 5-methylcytosyl group, an 8-oxoguanyl group, and a hypoxanthinyl group.

In Z, any protecting group can be bonded to the polar group of the base. Typical examples thereof can include groups which can be used as a protecting group for a primary amino group and a carbonyl group. Examples of the protecting group for a primary amino group can include a pivaloyl group, a trifluoroacetyl group, a phenoxyacetyl group, a 4-isopropylphenoxyacetyl group, an acetyl group, a benzoyl group, an isobutyryl group, and a dimethylformamidinyl group. Among these, a phenoxyacetyl group, a 4-isopropylphenoxyacetyl group, an acetyl group, a benzoyl group, an isobutyryl group, and a dimethylformamidinyl group are preferred. When a carbonyl group is protected, methanol, ethylene glycol, or 1,3-propane diol, etc. can be reacted with the carbonyl group to form acetal. The protecting group for the carbonyl group may not be introduced in some cases.

The oligonucleotide synthesis method according to the present invention is conducted according to a phosphoramidite method by use of the hydrophobic group-bonded nucleoside represented by Formula (1) as the starting raw material.

Namely, the oligonucleotide synthesis method according to the present invention comprises a step of sequentially condensing and oxidizing a nucleoside phosphoramidite compound (condensation and oxidation step) in the presence of an acid/azole complex compound by use of the hydrophobic group-bonded nucleoside as the starting raw material, wherein in the condensation reaction, the hydrophobic group-bonded nucleoside or hydrophobic group-bonded oligonucleotide and the nucleoside phosphoramidite compound are preliminarily dissolved in a non-polar solvent, and the resulting solution is contacted with the acid/azole complex compound or a solution containing the complex compound.

The method according to the present invention will now be described with reference to the initial condensation and oxidation step as an example.

(1-3)

where $R^1$, $R^2$, $R^3$, $R^4$, $R^5$, $R^6$, n, X, and Z represent the same as above; Y represents a protecting group deprotectable under an acidic condition; and $Z^1$ represents an adenyl group, a guanyl group, a cytosyl group, a thyminyl group, a uracil group, or a derivative of the nucleic acid base having a polar group optionally protected by a protecting group.

In the first step, the starting raw material, i.e., Hydrophobic group-bonded nucleoside (1) is condensed (coupled) with Nucleoside phosphoramidite compound (A) in the presence of Acid/azole complex compound (B).

The reagents are each added to the reaction system such that the hydrophobic group-bonded nucleoside and the nucleoside phosphoramidite compound are preliminarily dissolved in a non-polar solvent, and the resulting solution is contacted with the acid/azole complex compound or a solution containing the complex compound.

Namely, the hydrophobic group-bonded nucleoside should not be contacted with the acid/azole complex compound before the hydrophobic group-bonded nucleoside contacts with the nucleoside phosphoramidite compound.

As shown in the Examples later, if the hydrophobic group-bonded nucleoside is contacted with the acid/azole complex compound, and then with the nucleoside phosphoramidite compound to perform a reaction, coupling efficiency reduces more significantly than in the method according to the present invention. This tendency significantly appears in synthesis of RNA (Examples 1 to 3, Comparative Examples 1 to 3).

Such a method of preliminarily contacting the nucleoside phosphoramidite compound with the acid/azole complex compound is not preferred because reaction active species of phosphoramidite and the acid/azole complex compound are first generated, and the active species may be unintendedly degraded while the solution is continuously being flowed. In this case, degradation of the active species is not preferred because the reaction environment for the hydrophobic group-bonded nucleoside and the reaction active species of phosphoramidite and the acid/azole complex compound is no longer constant, resulting in difficulties in continuous preparation of the reaction product with a small amount of the reagent to be added at stable coupling yield.

In addition of the reagents into the reaction system, the solution prepared by preliminarily dissolving the hydrophobic group-bonded nucleoside and the nucleoside phosphoramidite compound in a non-polar solvent may be contacted with the acid/azole complex compound or a solution containing the complex compound. The reagent may be added by one of the following addition methods: a premixing method of dissolving the hydrophobic group-bonded nucleoside and the nucleoside phosphoramidite compound in a non-polar solvent in a reaction container, and then adding and mixing the acid/azole complex compound or a solution containing the complex compound with the solution in the same reaction container; or a two-solution mixing method of separately preparing a dissolution solution of the hydrophobic group-bonded nucleoside and the nucleoside phosphoramidite compound in a non-polar solvent and a dissolution solution of the acid/azole complex compound in a non-polar solvent, and then mixing these solutions.

The non-polar solvent is preferably at least one selected from the group consisting of dichloromethane, dichloroethane, chloroform, tetrahydrofuran, benzene, toluene, hexane, cyclohexane, and ethyl acetate, more preferably dichloromethane. These non-polar solvents improve the solubility of the hydrophobic group-bonded nucleoside in the hydrophobic group-bonded nucleoside solution, and can establish a strong hydrophobic environment.

As the starting raw material, the hydrophobic group-bonded nucleoside represented by Formula (1) wherein the hydroxyl group bonded to the carbon atom at the 5th-position of the pentose residue is protected by a protecting group deprotectable under an acidic condition can be used by properly deprotecting the hydroxyl group. Examples of the protecting group include those used as a protecting group for a hydroxyl group, such as a methyl group, a tert-butyl group, a methoxymethyl group, a 2-tetrahydropyranyl group, an ethoxyethyl group, a trimethylsilyl group, a triethylsilyl group, a tert-butyldimethylsilyl group, a triisopropylsilyl group, dimethoxytrityl groups such as a 1,1-bis(4-methoxyphenyl)-1-phenylmethyl group, and monomethoxytrityl groups such as a 1-(4-methoxyphenyl)-1,1-diphenylmethyl group.

The deprotection reaction is conducted with an acidic solution, and is terminated by addition of a reducing agent. Examples of acids used for the acidic solution can include trichloroacetic acid, dichloroacetic acid, monochloroacetic acid, and trifluoroacetic acid. Among these, dichloroacetic acid is preferred. Examples of a scavenger for a free protecting group can include methanol, triethylsilane, triisopropylsilane, anisole, thioanisole, and ethanedithiol, and methanol and triethylsilane are preferred.

Examples of the acid/azole complex compound can include 5-benzylmercapto-1H-tetrazole, 5-ethylthio-1H-tetrazole, 4,5-dicyanoimidazole, 1H-tetrazole, benzimidazolium triflate, and N-phenylbenzimidazolium triflate. Among these, usually, 5-benzylmercapto-1H-tetrazole, 5-ethylthio-1H-tetrazole, 4,5-dicyanoimidazole, and 1H-tetrazole are domestically commercially available in a typical form of a dissolution in a polar solvent such as acetonitrile. Usually, benzimidazolium triflate, N-phenylbenzimidazolium triflate, and the like, which are not commercially available in a form of a dissolution in a polar solvent such as acetonitrile, are dissolved in a polar solvent such as acetonitrile immediately before use. The method according to the present invention preferably uses a mixture of an acid/azole complex compound dissolved in the non-polar solvent, preferably the same solvent used to dissolve the hydrophobic group-bonded nucleoside and the nucleoside phosphoramidite compound and an acid/azole complex compound dissolved in a polar solvent such as acetonitrile.

The nucleoside phosphoramidite compound can be properly selected according to the characteristics of a target hydrophobic group-bonded oligonucleotide. Both of a ribonucleoside phosphoramidite compound and a deoxyribonucleoside phosphoramidite compound having protected hydroxyl groups at the 2nd-position and 5th-position of the pentose residue can optionally be used. Those having, for the base, an adenyl group, a guanyl group, a cytosyl group, a thyminyl group, a uracil group, an 8-bromoadenyl group, an 8-bromoguanyl group, a 5-bromocytosyl group, a 5-iodocytosyl group, a 5-bromouracil group, a 5-iodouracil group, a 5-fluorouracil group, a 5-methylcytosyl group, an 8-oxoguanyl group, a hypoxanthinyl group, and the like having a polar group optionally bonded to a protecting group can be used.

In the nucleoside phosphoramidite compound, the protecting groups for the hydroxyl groups at the 2nd-position and at the 5th-position of the pentose residue and the polar group of the base (Y and $Z^1$ of the compound (A)) can be the same as those for the corresponding groups of the hydrophobic group-bonded nucleoside compound.

The condensation reaction may be conducted on a typical condition used in the phosphoramidite method, for example, at 15 to 40° C., preferably at 35 to 40° C. for 10 to 30 minutes, preferably for 10 to 15 minutes. In the condensation reaction, all of the reagents and solvents, including the support, needed in the oligonucleotide synthesis can be fed in forms of liquid to conduct a liquid-phase reaction with high coupling efficiency. Accordingly, the condensation reaction can be conducted in a fluid with a known flow synthetic system.

Figure 1:
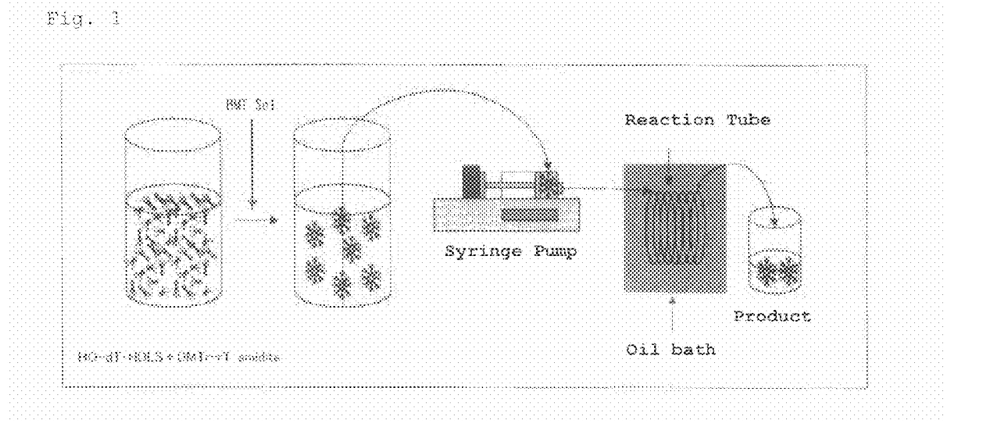
FIG. 1 is a conceptual diagram illustrating a premixing flow synthetic system.
Figure 2:
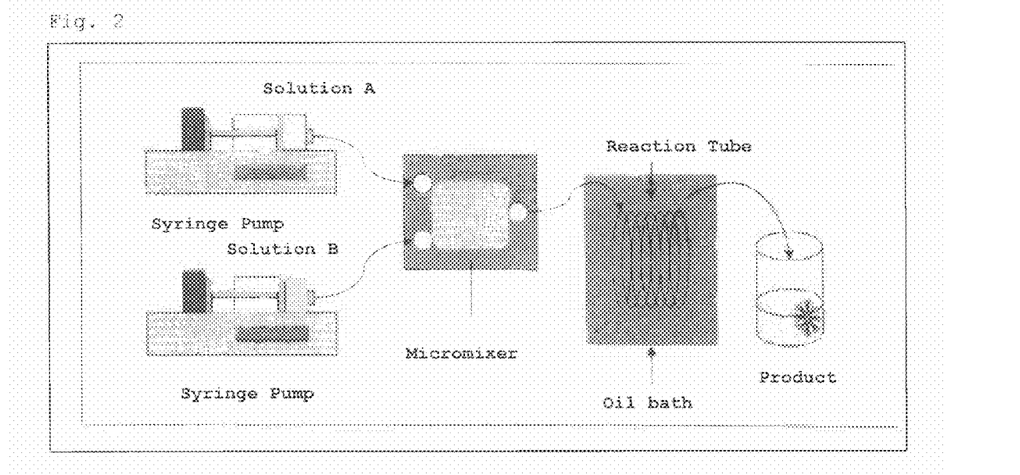
FIG. 2 is a conceptual diagram illustrating a two-solution mixing flow synthetic system.
Figure 3:
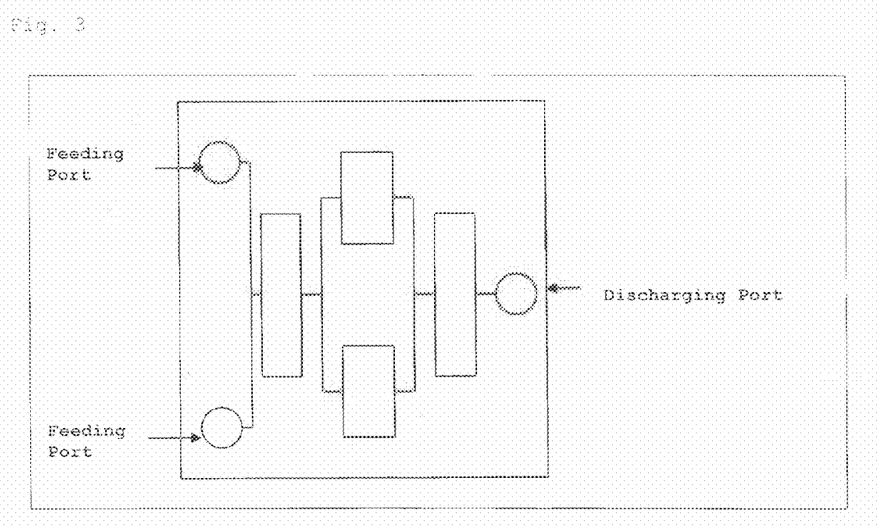
FIG. 3 is a plan view illustrating a multi-stage colliding micromixer.
Figure 4:
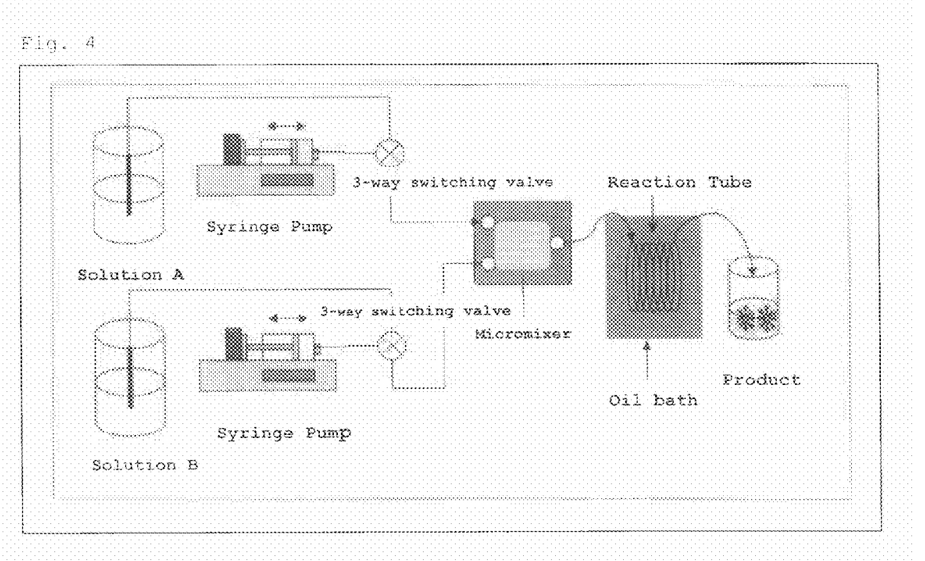
FIG. 4 is a conceptual diagram illustrating a flow synthetic system including a syringe pump by a method of continuously feeding and discharging a reaction solution.

Namely, the condensation reaction can continuously be conducted with a flow synthetic apparatus including a sample feeding flow path for feeding a sample, a reaction flow path for conducting a reaction, an optional mixing unit for guiding the sample feeding flow path to the reaction flow path, an optional unit for feeding a liquid to the flow paths continuously, an optional unit for adjusting the reaction temperature, and the like (see FIGS. 1, 2, and 4).

Any known units, tools, and materials are used for the respective members of the apparatus.

Examples of the material and shape for the reaction flow path include tubes composed of fluorine resins such as perfluoroalkoxy alkane (PFA) and synthetic resins such as vinyl chloride resins, polyamide resins, and aromatic polyether ketone resins; and metal tubes composed of stainless steel, copper or alloys thereof, and titanium or alloys thereof. Examples of the liquid feeding unit include pumps for feeding a reaction solution typically used in this field, such as syringe pumps, plunger pumps, diaphragm pumps, and gear pumps. Examples of the mixing unit for guiding the sample feeding flow path to the reaction flow path include multi-stage colliding micromixers.

The inner diameter of the flow path may be properly selected from the range of usually 0.1 to 1.0 mm to conduct the reaction in a liquid. The inner diameter is preferably selected from the range of 0.2 to 1.0 mm. The flow rate of the liquid to be continuously fed, which varies according to the length, the inner diameter, and the like of the flow path as the reaction field, is, for example, usually 0.1 to 1.0 ml/min, preferably 0.1 to 0.2 ml/min.

When the reaction is conducted in the flow mode, the amount of production can be freely varied, in principle, only by an increase or decrease of the amounts of two reaction solutions. The place for the reaction is disposed downstream of the micromixer, and predetermined reaction efficiency can be always maintained with a small amount of the reagent to be added. These are significantly advantageous compared to a liquid-phase synthesis method conducted in a flask in a batch mode or a solid-phase synthesis method.

In a second stage of the condensation and oxidation step, a compound represented by Formula (1-2) is dissolved in the non-polar solvent, and an oxidizing agent is added to initiate an oxidation reaction. A compound represented by Formula (1-3) is prepared. Examples of the oxidizing agent can include a mixture of iodine/water/pyridine, a solution of tert-butyl peroxide/toluene, and a solution of 2-butanone peroxide/methylene chloride. Specific examples of a reaction method can include a method of preparing a dissolution solution of the compound represented by Formula (1-2) in dichloromethane or the like, and adding a mixed solution of iodine/water/tetrahydrofuran/pyridine to the dissolution solution.

The compound represented by Formula (1-2) and generated in the first stage and the compound represented by Formula (1-3) can be crystallized to be separated and recovered in a "separation stage" described later.

The reaction in the condensation and oxidation step has been described in detail with reference to the initial condensation and oxidation reaction as an example. The same reaction is sequentially repeated to synthesize hydrophobic group-bonded oligonucleotide having a structure in which the carbon atom at the 5th-position of a pentose residue of a nucleoside residue bonded to the hydrophobic group-bonded nucleoside is continuously bonded through a phosphate group to the carbon atom at the 3rd-position of a pentose residue having an adjacent nucleoside residue on the 5'-terminal side of the hydrophobic group-bonded oligonucleotide.

After the condensation and oxidation step is terminated, the protecting group bonded to the hydrophobic group-bonded oligonucleotide is deprotected. The protecting group can be properly deprotected by a method well known to persons skilled in the art according to the type and property of the protecting group bonded to the hydrophobic group-bonded oligonucleotide.

For example, when a tert-butyldimethylsilyl group is used as a protecting group for the hydroxyl group at the 2nd-position of the pentose residue, the tert-butyldimethylsilyl group can be deprotected by a reaction with a mixed solution of N-methylpyrrolidone/triethylamine.3HF/triethylamine at 60° C. for 90 minutes. When one of a phenoxy acetyl group, a 4-isopropylphenoxyacetyl group, an acetyl group, a benzoyl group, and an isobutyryl group is used as a protecting group for the polar group of the base, the protecting group can be deprotected by a reaction with a solution of ammonia:ethanol=3:1 at 80° C. for 90 minutes. The deprotection reaction of the protecting group for the hydroxyl group at the 5th-position of the pentose residue may be conducted by the same method as above.

The hydrophobic group (HDLS) of the hydrophobic group-bonded nucleoside portion can also be eliminated by the same procedure. For example, the hydrophobic group (HDLS) including the linker portion connecting the nucleoside to the HDLS can be eliminated simultaneously by a reaction with a solution of ammonia:ethanol=3:1 at 80° C. for 90 minutes.

The method according to the present invention may have a step of separating the product after the chemical reaction at each of the stages. Examples of the separating method can include a method by varying a solution temperature and/or a solution composition. As described above, the present invention uses the hydrophobic group-bonded nucleoside represented by Formula (1). The respective reaction products can be readily separated and recovered by the method of varying a solution temperature and/or a solution temperature.

Examples of the method of varying a solution temperature can include a method of cooling a reaction solution. Specifically, for example, when a mixed solution of dichloromethane/methanol or a mixed solution of dichloromethane/acetonitrile is used as a solvent to dissolve an intermediate product in the hydrophobic group-bonded oligonucleotide synthetic method, the mixed solution can be cooled to 0° C. or less to crystallize the intermediate product.

Examples of the method of varying a solution composition can include a method of preparing a dissolution solution of an intermediate product of the hydrophobic group-bonded oligonucleotide synthetic method in a non-polar solvent, and adding a solvent having high affinity with the non-polar solvent. In this case, the reaction solution keeps one phase without separation into phases.

The solvent having high affinity with the non-polar solvent may be the same as or different from the solvent used as the non-polar solvent. For example, when dichloromethane or tetrahydrofuran is used as the non-polar solvent, acetonitrile, dimethylformamide, or methanol can be used.

Another preferred examples of the method of varying a solution composition can include a known method of condensing a dissolution solution of a reaction product of the hydrophobic group-bonded oligonucleotide synthetic method in a non-polar solvent.

Examples of a suitable separating method can include a method of adding acetonitrile to a dissolution solution of a reaction product in dichloromethane, vaporizing the solvent to condense the solution, cooling the condensed solution to crystallize the reaction product in dichloromethane, and separating the crystallized product by suction filtration; and a method of adding methanol to a dissolution solution of a reaction product in dichloromethane, vaporizing the solvent to condense the solution, and centrifuging or separating the reaction product.

EXAMPLES

Production Example 1

Synthesis of Hydrophobic Group-Bonded Nucleoside

558.8 mg (3 mmol) of 4-butoxy carbonyl piperazine, 405.4 mg (3 mmol) of 1-hydroxybenzotriazole (HOBO, 1.1378 g (1 mmol) of 2-(1H-1-benzotriazolyl)-1,1,3,3-tetramethyluronium hexafluorophosphate (HBTU), and 523 μl (3 mmol) of N,N-diisopropylethylamine (DIEA) were added to 927.6 mg (1 mmol) of 3,4,5-tris(octadecyloxy)benzoic acid to synthesize 3,4,5-tris(octadecyloxy)benzoic acid-4-butoxycarbonylpiperazine. 4 N hydrochloric acid was acted on the product to synthesize 3,4,5-tris(octadecyloxy)benzoic acid-piperazine hydrochloride.

5.08 g of 5'-O-(1,1-bis(4-methoxyphenyl)-1-phenylmethyl)thymidine having a thyminyl group whose hydroxyl group at the 5th-position was protected by a dimethoxytrityl group was dissolved in a proper amount of dichloromethane. 1.52 g of succinic anhydride and 10 mL of triethylamine were added, and the solution was stirred. After the completion of the reaction was checked by thin-layer chromatography, the product and a 0.2 M triethylamine phosphate aqueous solution were placed in a separating funnel to recover an organic layer. The organic layer was condensed and dried with an evaporator to prepare 3'-O-succinyl-5'-O-(1,1-bis(4-methoxyphenyl)-1-phenylmethyl)thymidine having a thyminyl group whose hydroxyl group at the 5th-position was protected by a dimethoxytrityl group.

500 mg of 3,4,5-tris(octadecyloxy)benzoic acid-piperazine hydrochloride was dissolved in 50 mL of dichloromethane, and 644 mg of 3'-succinyl-5'-O-(1,1-bis(4-methoxyphenyl)-1-phenylmethyl)thymidine having a thyminyl group whose hydroxyl group at the 5th-position was protected by a dimethoxytrityl group, 1137 mg of 2-(1H-1-benzotriazolyl)1,1,3,3-tetramethyluronium hexafluorophosphate (HBTU), and 510 μl of diisopropylethylamine were added, and were stirred. After the completion of the reaction was checked by thin-layer chromatography, the reaction solution was condensed with an evaporator, and was subjected to suction filtration to prepare 5'-O-(4,4'-dimethoxytrityl)thymidine-3'-O-succinylpiperazine-4-(1-carbonyl-3,4,5-tris (octadecyloxy).

Then, a dissolution solution of 324.4 mg of 5'-O-(4,4'-dimethoxytrityl)thymidine-3'-O-succinylpiperazine-4-(1-carbonyl-3,4,5-tris(octadecyloxy) (100 μmol) in 10 mL of dichloromethane and 10 mL of 3% trichloroacetic acid/dichloromethane solution were placed in an eggplant-shaped flask container, and were uniformly stirred. After the reaction solution was left at room temperature for 5 minutes, methanol was added. Part of the reaction solution was extracted to check the completion of the reaction by thin-layer chromatography. The reaction solution was transferred from the eggplant-shaped flask container to an evaporator to be condensed. The condensed solution was subjected to suction filtration with a Kiriyama funnel to prepare Compound 1 represented by the following formula (hereinafter, also referred to as "HO-dT-HDLS"):

(Compound 1)

$Z^2$: thyminyl group

Example 1

Synthesis of DMT-dT-dT-HDLS (1)

Compound 2 represented by the following formula (hereinafter, also referred to as "DMT-dT-dT-HDLS") was synthesized with a premixing flow synthetic system shown in FIG. 1.

1 mg of the product was dissolved in 1 mL of chloroform, and the solution was analyzed by HPLC on the following conditions. Coupling efficiency was calculated from the integrated value of the peak area determined by HPLC at absorption at UV=258 nm.

<HPLC Apparatus and Setting>
  system: waters alliance e2695,
  column: inertsil 100 A (5 μm, 4.6φ×150 mm, GL Sciences Inc.)
  column temperature: 30° C.,
  flow rate: 1.0 mL/min, mobile phase (A): chloroform, eluent (B): methanol
  time for analysis: 30 minutes, gradient: 1% (0 min)--->5% (30 min)

(Compound 2)

$Z^2$: thyminyl group
$Y'$: 1,1-bis(4-methoxyphenyl)-1-phenylmethyl group

1) Configuration of Apparatus syringe: 25 mL gas-tight syringe (manufactured by Hamilton Company)
syringe pump (manufactured by HARVARD Apparatus, APPARATUS 11 PLUS)
Teflon (registered trademark) tube (inner diameter: 1 mm, length: 3 m)
oil bath (manufactured by AS ONE Corporation, HOA-50D) 2) Method
i) Preparation of Solution
  25 mL of dehydrated dichloromethane (KANTO CHEMICAL CO., INC.) was added to HO-dT-HDLS prepared in Production Example 1 (Compound 1)(132 mg, 0.1 mmol), and HO-dT-HDLS was dissolved in a 100 mL two-necked recovery flask. 100 mg of a molecular sieve 3 A (Sigma-Aldrich Co., LLC.) was added, and the solution was stirred at room temperature for 5 minutes. After 5 minutes passed, 149 mg (0.2 mmol) of DMTr-dT Amidite (Thermo Fisher Scientific Inc.) was added to the solution, and was stirred for 35 minutes.
ii) Coupling
  5 mL of a BMT Solution (0.25 M acetonitrile solution, Wako Pure Chemical Industries, Ltd.) was added to the mixed solution of HO-dT-HDLS (Compound 1) and DMTr-dT Amidite prepared above, and was stirred for 1 minute.

The solution was all extracted with a 25 mL gas-tight syringe, and was flowed with a syringe pump into a tube to feed to the coupling reaction at a flow rate of 0.1 ml/min and at a temperature of 35° C. The reaction solution was received in a receiver.
iii) Oxidation
  Then, 10 mL of a 0.67% 2-butanoneperoxide/dichloromethane solution was added to the resulting reaction solution, and was stirred for 10 minutes.
iv) Separation and Refining
  After the reaction was completed, 20 mL of methanol was added, and the reaction solvent (dichloromethane) was distilled off with an evaporator. The condensing operation was terminated when a white solid product began generating, and the reaction solution was left at room temperature for 15 minutes. The reaction solution was subjected to suction filtration with a Kiriyama funnel to prepare a residue (purity: 99%, recovering rate: 95%).

3) Coupling Efficiency: 99%

Example 2

Synthesis of DMT-dT-dT-HDLS (2)

DMT-dT-dT-HDLS (Compound 2) was synthesized in the same manner as in Example 1 with a two-solution mixing flow synthetic system shown in FIG. 2. The product was analyzed by HPLC in the same manner as in Example 1 to calculate coupling efficiency.

1) Configuration of Apparatus (See FIG. 2)

syringe: 25 mL gas-tight syringe (manufactured by Hamilton Company)
syringe pump (manufactured by HARVARD Apparatus, APPARATUS 11 PLUS)
Teflon (registered trademark) tube (inner diameter: 1 mm, length: 3 m)
oil bath (manufactured by AS ONE Corporation, HOA-50D)

micromixer (statics type, flow path diameter: 0.2 mm, flow path volume: 19.95 μL, manufactured by YMC CO., LTD.)

2) Method i) Preparation of Solution

Solution A containing HO-dT-HDLS (Compound 1) and DMTr-dT Amidite and Solution B containing BMT Solution were prepared as shown in Table 1.

TABLE 1

| Solution A | | Solution B | |
|---|---|---|---|
| HO-dT-HDLS | 0.1 mmol | 0.25M BMT Sol. | 5.0 mL |
| DMTr-dT amidite | 0.2 mmol | | |
| Dichloromethane | 12.5 mL | Dichloromethane | 7.5 mL |

(Solution A)

132 mg (0.1 mmol) of HO-dT-HDLS prepared in Production Example 1 (Compound 1), 149 mg (0.2 mmol) of DMTr-dT Amidite (Thermo Fisher Scientific Inc.), and 12.5 mL of dehydrated dichloromethane (KANTO CHEMICAL CO., INC.) were dissolved in a 100 mL two-necked recovery flask, to which then was added 100 mg of a molecular sieve 3 A (Sigma-Aldrich Co., LLC.), and the resulting solution was stirred at room temperature for 40 minutes. (Solution B)

5 mL of BMT Solution (0.25 M acetonitrile solution, Wako Pure Chemical Industries, Ltd.) and 7.5 mL of dehydrated dichloromethane (KANTO CHEMICAL CO., INC.) were added to a 100 mL two-necked recovery flask, and were stirred.

ii) Coupling

Solution A and Solution B were each all extracted with a 25 mL gas-tight syringe. These solutions were flowed with syringe pumps into tubes, and were mixed with a micromixer. These solutions were reacted inside of a reaction tube at a flow rate of 0.1 ml/min and at a temperature of 35° C. After the reaction was completed, the reaction product was received in a receiver.

iii) Oxidation

Then, 10 mL of a 0.67% 2-butanoneperoxide/dichloromethane solution was added to the resulting reaction solution, and was stirred for 10 minutes.

iv) Separation and Refining

After the reaction was completed, 20 mL of methanol was added, and the reaction solvent (dichloromethane) was distilled off with an evaporator. The condensing operation was terminated when a white solid product began generating, and the reaction solution was left at room temperature for 15 minutes. The reaction solution was subjected to suction filtration with a Kiriyama funnel to prepare a residue.

3) Coupling Efficiency: >99%

Comparative Example 1

Synthesis of DMT-dT-dT-HDLS

Solution A and Solution B shown below were prepared with the same two-solution mixing flow synthetic system as in Example 2. DMT-dT-dT-HDLS (Compound 2) was synthesized in the same manner as in Example 2. The product was analyzed by HPLC in the same manner as in Example 1 to calculate coupling efficiency.

1) Preparation of Solution

Solution A containing HO-dT-HDLS (Compound 1) and BMT Solution and Solution B containing DMTr-dT Amidite were prepared as shown in Table 2.

TABLE 2

| Solution A | | Solution B | |
|---|---|---|---|
| HO-dT-HDLS | 0.1 mmol | DMTr-dT amidite | 0.2 mmol |
| 0.25M BMT Sol. | 5 mL | | |
| Dichloromethane | 7.5 mL | Dichloromethane | 12.5 mL |

(Solution A)

132 mg (0.1 mmol) of HO-dT-HDLS (Compound 1), 5 mL of BMT Solution (0.25 M acetonitrile solution, Wako Pure Chemical Industries, Ltd.), and 7.5 mL of dehydrated dichloromethane (KANTO CHEMICAL CO., INC.) were dissolved in a 100 mL two-necked recovery flask, to which then was added 100 mg of a molecular sieve 3 A (Sigma-Aldrich Co., LLC.), and the resulting solution was stirred at room temperature for 40 minutes.

(Solution B)

149 mg (0.2 mmol) of DMTr-dT Amidite (Thermo Fisher Scientific K.K.) was dissolved in 12.5 mL of dehydrated dichloromethane (KANTO CHEMICAL CO., INC.) in a 100 mL two-necked recovery flask, to which then was added 100 mg of a molecular sieve 3 A (Sigma-Aldrich Co., LLC.), and the resulting solution was stirred for 40 minutes.

2) Coupling Efficiency: 98%

At a coupling efficiency of 98%, assume that 20 bases extend. Then, the estimated proportion of the target product can be $0.98^{20} \times 100 = 66.7(\%)$. At a coupling efficiency of 99%, $0.99^{20} \times 100 = 81.8(\%)$ from the same calculation, and the difference is 15.1%.

A difference of only 1% in coupling efficiency may significantly affect the amount of the target oligonucleotide to be recovered. Accordingly, the coupling efficiency is most preferably 99% or more.

Example 3

Synthesis of DMT-rU-dT-HDLS

Compound 3 (hereinafter, also referred to as "DMT-rU-dT-HDLS") represented by the following formula was synthesized in the same two-solution mixing flow synthetic system as in Example 2. The product was analyzed by HPLC in the same manner as in Example 1 to calculate coupling efficiency.

(Compound 3)

$Z^2$: thyminyl group, $Z^3$: uracil group
Y': 1,1-bis(4-methoxyphenyl)-1-phenylmethyl group
TBDMS: tert-butyldimethylsilyl group 1) Configuration of Apparatus (See FIG. 2)
   syringe: 25 mL gas-tight syringe (manufactured by Hamilton Company)
   syringe pump (manufactured by HARVARD Apparatus, APPARATUS 11 PLUS)
   Teflon (registered trademark) tube (inner diameter: 1 mm, length: 3 m)
   oil bath (manufactured by AS ONE Corporation, HOA-50D)
   micromixer (statics type, flow path diameter: 0.2 mm, flow path volume: 19.95 manufactured by YMC CO., LTD.)
2) Method
i) Preparation of Solution
   Solution A containing HO-dT-HDLS (Compound 1) and DMTr-rU Amidite and Solution B containing BMT Solution were prepared as shown in Table 3.

TABLE 3

| Solution A | | Solution B | |
|---|---|---|---|
| HO-dT-HDLS | 0.1 mmol | 0.25M BMT Sol. | 5.0 mL |
| DMTr-rU amidite | 0.2 mmol | | |
| Dichloromethane | 12.5 mL | Dichloromethane | 7.5 mL |

(Solution A)
132 mg (0.1 mmol) of HO-dT-HDLS (Compound 1), 172 mg (0.2 mmol) of DMTr-rU Amidite (Glen Research Corp.), and 12.5 mL of dehydrated dichloromethane (KANTO CHEMICAL CO., INC.) were dissolved in a 100 mL two-necked recovery flask, to which then was added 100 mg of a molecular sieve 3 A (Sigma-Aldrich Co., LLC.), and the resulting solution was stirred at room temperature for 40 minutes.
(Solution B)
5 mL of BMT Solution (0.25 M acetonitrile solution, Wako Pure Chemical Industries, Ltd.) and 7.5 mL of dehydrated dichloromethane (KANTO CHEMICAL CO., INC.) were added to a 100 mL two-necked recovery flask, and were stirred.
ii) Coupling
   Solution A and Solution B were each all extracted with a 25 mL gas-tight syringe. These solutions were flowed into a tube with a syringe pump, and were mixed with a micromixer to be reacted inside of the reaction tube at a flow rate of 0.1 ml/min and at a temperature of 35° C. After the reaction was completed, the reaction product was received in a receiver.
iii) Oxidation
   Then, 10 mL of a 0.67% 2-butanoneperoxide/dichloromethane solution was added to the resulting reaction solution, and was stirred for 10 minutes.
iv) Separation and Refining
   After the reaction was completed, 20 mL of methanol was added, and the reaction solvent (dichloromethane) was distilled off with an evaporator. The condensing operation was terminated when a white solid product began generating. The reaction solution was left at room temperature for 15 minutes. The reaction solution was subjected to suction filtration with a Kiriyama funnel to prepare a residue.
3) Coupling Efficiency: 99%

Comparative Example 2

Synthesis of DMT-rU-dT-HDLS

Solution A and Solution B shown below were prepared with the same two-solution mixing flow synthetic system as in Example 3. DMT-rU-dT-HDLS (Compound 3) was synthesized in the same manner as in Example 3. The product was analyzed by HPLC in the same manner as in Example 1 to calculate coupling efficiency.

1) Preparation of Solution

Solution A containing HO-dT-HDLS (Compound 1) and BMT Solution and Solution B containing DMTr-rU Amidite were prepared as shown in Table 4.

TABLE 4

| Solution A | | Solution B | |
|---|---|---|---|
| HO-dT-HDLS | 0.1 mmol | DMTr-rU amidite | 0.2 mmol |
| 0.25M BMT Sol. | 5 mL | | |
| Dichloromethane | 7.5 mL | Dichloromethane | 12.5 mL |

(Solution A)
132 mg (0.1 mmol) of HO-dT-HDLS (Compound 1), 5 mL of BMT Solution (0.25 M acetonitrile solution, Wako Pure Chemical Industries, Ltd.), 7.5 mL of dehydrated dichloromethane (KANTO CHEMICAL CO., INC.) were dissolved in a 100 mL two-necked recovery flask, to which then was added 100 mg of a molecular sieve 3 A (Sigma-Aldrich Co., LLC.), and the resulting solution was stirred at room temperature for 40 minutes.
(Solution B)

172 mg (0.2 mmol) of DMTr-rU Amidite (Glen Research Corp.) was dissolved in 12.5 mL of dehydrated dichloromethane (KANTO CHEMICAL CO., INC.) in a 100 mL two-necked recovery flask, to which then was added 100 mg of a molecular sieve 3 A (Sigma-Aldrich Co., LLC.), and the resulting solution was stirred for 40 minutes.

2) Coupling Efficiency: 70%

Comparative Example 3

Synthesis of DMT-rU-dT-HDLS

Solution A and Solution B shown in Table 5 were prepared with the same two-solution mixing flow synthetic system as in Example 3. DMT-rU-dT-HDLS (Compound 3) was synthesized in the same manner. The product was analyzed by HPLC in the same manner as in Example 1 to calculate coupling efficiency.
1) Preparation of Solution Solution A containing HO-dT-HDLS (Compound 1) and BMT Solution and Solution B containing DMTr-rU Amidite were prepared as shown in Table 4.

TABLE 5

| Solution A | | Solution B | |
|---|---|---|---|
| HO-dT-HDLS | 0.1 mmol | DMTr-rU amidite | 0.6 mmol |
| 0.25M BMT Sol. | 5 mL | | |
| Dichloromethane | 7.5 mL | Dichloromethane | 12.5 mL |

(Solution A)

132 mg (0.1 mmol) of HO-dT-HDLS (Compound 1), 5 mL of BMT Solution (0.25 M acetonitrile solution, Wako Pure Chemical Industries, Ltd.), and 7.5 mL of dehydrated dichloromethane (KANTO CHEMICAL CO., INC.) were dissolved in a 100 mL two-necked recovery flask, to which then was added 100 mg of a molecular sieve 3 A (Sigma-Aldrich Co., LLC.), and the resulting solution was stirred at room temperature for 40 minutes.
(Solution B)

517 mg (0.6 mmol) of DMTr-rU Amidite (Glen Research Corp.) was dissolved in 12.5 mL of dehydrated dichloromethane (KANTO CHEMICAL CO., INC.) in a 100 mL two-necked recovery flask, to which then was added 100 mg of a molecular sieve 3 A (Sigma-Aldrich Co., LLC.), and the resulting solution was stirred for 40 minutes.
2) Coupling Efficiency: 99%

When the solution of HO-dT-HDLS (Compound 1) and BMT Solution was prepared, about 6 equivalents of the amidite monomer (BMT Solution) relative to HO-dT-HDLS was needed to attain high coupling efficiency.

Example 4

Synthesis of DMT-dT-dT-HDLS (3)

Compound 2 (DMT-dT-dT-HDLS) was synthesized with a two-solution mixing flow synthetic system (continuous mass-synthetic system) shown in FIG. 4 in the same manner as in Example 1. The product was analyzed by HPLC in the same manner as in Example 1 to calculate coupling efficiency.
1) Configuration of Apparatus (See FIG. 4)
   syringe: 25 mL gas-tight syringe (manufactured by Hamilton Company)
   syringe pump (manufactured by HARVARD Apparatus, APPARATUS 11 PLUS)
   Teflon (registered trademark) tube (inner diameter: 1 mm, length: 3 m)
   3-way switching valve (manufactured by TOKYO RIKAKIKAI CO., LTD.)
   oil bath (manufactured by AS ONE Corporation, HOA-50D)
   micromixer (statics type, flow path diameter: 0.2 mm, flow path volume: 19.95 manufactured by YMC CO., LTD.)
2) Method
i) Preparation of Solution Solution A containing HO-dT-HDLS (Compound 1) and DMTr-dT Amidite and Solution B containing BMT Solution were prepared as shown in Table 6.

TABLE 6

| Solution A | | Solution B | |
|---|---|---|---|
| HO-dT-HDLS | 0.5 mmol | 0.25M BMT Sol. | 25 mL |
| DMTr-rT amidite | 1.0 mmol | | |
| Dichloromethane | 62.5 mL | Dichloromethane | 37.5 mL |

(Solution A)

660 mg (0.5 mmol) of HO-dT-HDLS (Compound 1), 744 mg (1.0 mmol) of DMTr-dT Amidite (Thermo Fisher Scientific K.K.), and 62.5 mL of dehydrated dichloromethane (KANTO CHEMICAL CO., INC.) were dissolved in a 100 mL two-necked recovery flask, to which then was added 500 mg of a molecular sieve 3 A (Sigma-Aldrich Co., LLC.), and the resulting solution was stirred at room temperature for 40 minutes.
(Solution B)

Figure 5:
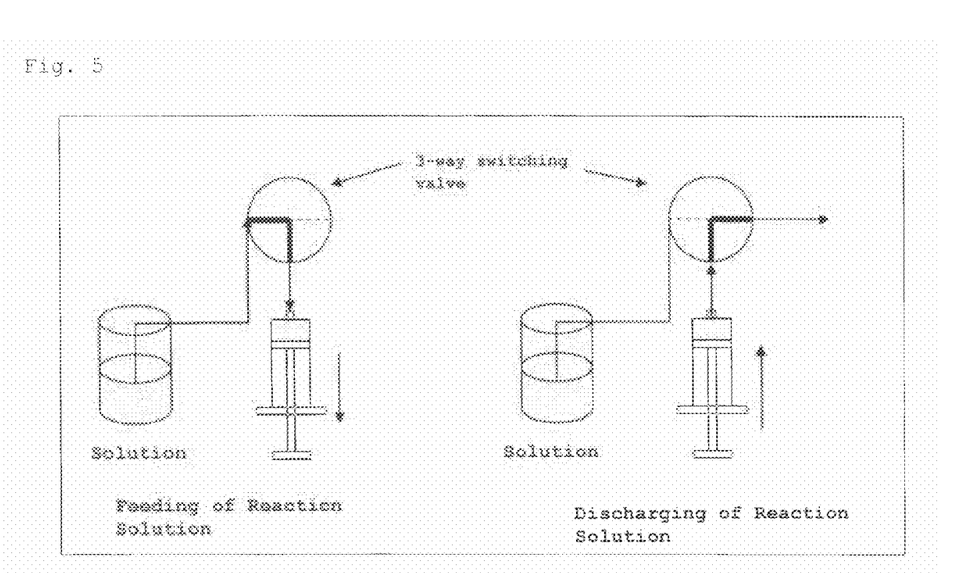
FIG. 5 is a conceptual diagram illustrating a mechanism to feed and discharge a reaction solution with a switching valve.

25 mL of BMT Solution (0.25 M acetonitrile solution, Wako Pure Chemical Industries, Ltd.) and 37.5 mL of dehydrated dichloromethane (KANTO CHEMICAL CO., INC.) were added to a 100 mL two-necked recovery flask, and were stirred.
ii) Coupling Solution A and Solution B were each suctioned with a 25 mL gas-tight syringe through the switching valve (see FIG. 5) in an amount of 12.5 mL. The valves were switched to the micromixer side. These solutions were flowed with the respective syringe pumps into the tubes, and were mixed with the micromixer. These solutions were reacted inside of the reaction tube at a flow rate of 0.1 ml/min and at a temperature of 35° C. After the reaction was completed, the reaction product was received in a receiver. This operation was repeated 5 times in total. A non-used receiver was used for each operation to receive the product.
iii) Oxidation Then, 10 mL of a 0.67% 2-butanoneperoxide/dichloromethane solution was added to the resulting reaction solution, and was stirred for 10 minutes. This operation was performed on the respective receivers.
iv) Separation and Refining After the reaction was completed, 20 mL of methanol was added, and the reaction solvent (dichloromethane) was distilled off with an evaporator. The condensing operation was terminated when a white solid product began generating, and the reaction solution was left at room temperature for 15 minutes. The reaction solution was subjected to suction filtration with a Kiriyama funnel to prepare a residue.

3) Coupling Efficiency

TABLE 7

| Flow | Coupling efficiency (%) |
|---|---|
| First operation | 99.63 |
| Second operation | 99.70 |
| Third operation | 99.58 |
| Fourth operation | 99.55 |
| Fifth operation | 99.59 |
| Average | 99.61 |
| Standard deviation | 0.06 |

The invention claimed is:

1. A method for synthesizing an oligonucleotide comprising: sequentially condensing and oxidizing a nucleoside phosphoramidite compound in the presence of an acid/azole complex compound using a starting raw material comprising a hydrophobic group-bonded nucleoside represented by Formula (1):

where $R^1$ represents an alkylene group having 1 to 12 carbon atoms; $R^2$ represents an alkylene group having 1 to 22 carbon atoms; $R^3$ and $R^4$ each independently represent an alkyl group having 1 to 22 carbon atoms, or $R^3$ and $R^4$ represent a divalent group in which they are bonded to each other to form a heterocycle together with adjacent nitrogen atoms and $R^2$, the heterocycle being represented by Formula (2):

where $R^7$ represents an alkyl group having 1 to 6 carbon atoms; m represents an integer of 0 or 1; and y represents an integer of 0 to 3;

$R^5$ represents a single bond or an alkylene group having 1 to 22 carbon atoms; $R^6$ each independently represents an alkyl group having 6 to 30 carbon atoms; n represents an integer of 2 to 6; X represents a hydrogen atom, a hydroxyl group, or a hydroxyl group protected by a protecting group; and Z represents an adenyl group, a guanyl group, a cytosyl group, a thyminyl group, a uracil group, or a derivative of the nucleic acid base having a polar group optionally protected by a protecting group;
wherein a condensation reaction is performed by preliminarily dissolving the hydrophobic group-bonded nucleoside or hydrophobic group-bonded oligonucleotide and the nucleoside phosphoramidite compound in a non-polar solvent, and contacting the resulting solution with the acid/azole complex compound or a solution containing the complex compound.

2. The method for synthesizing an oligonucleotide according to claim 1, wherein a dissolution solution of the hydrophobic group-bonded nucleoside or hydrophobic group-bonded oligonucleotide and the nucleoside phosphoramidite compound in a non-polar solvent and a dissolution solution of the acid/azole complex compound in a non-polar solvent are separately prepared, and are mixed.

3. The method for synthesizing an oligonucleotide according to claim 1, wherein a dissolution solution of the hydrophobic group-bonded nucleoside or hydrophobic group-bonded oligonucleotide and the nucleoside phosphoramidite compound in a non-polar solvent and a dissolution solution of the acid/azole complex compound in a non-polar solvent are separately fed into a flow path to continuously conduct the condensation reaction in the flow path.

4. A method for synthesizing an oligonucleotide, wherein the starting raw material hydrophobic group-bonded nucleoside is a compound represented by Formula (3):

where $R^{6'}$ each independently represents an alkyl group having 18 to 30 carbon atoms; $R^1$ represents an alkylene group having 1 to 12 carbon atoms; y represents an integer of 0 to 3; X represents a hydrogen atom, a hydroxyl group, or a hydroxyl group protected by a protecting group; and Z represents an adenyl group, a guanyl group, a cytosyl group, a thyminyl group, a uracil group, or a derivative of the nucleic acid base having a polar group optionally protected by a protecting group.

5. The method for synthesizing an oligonucleotide according to claim 4, wherein in Formula (3), $R^{6'}$ is an octadecyl group.

* * * * *